United States Patent [19]
Mui

[11] 3,957,844
[45] May 18, 1976

[54] PROCESS FOR MAKING MERCAPTO SUBSTITUTED SILICON COMPOUNDS

[75] Inventor: Jeffrey Y. P. Mui, Ossining, N.Y.

[73] Assignee: Union Carbide Corporation, New York, N.Y.

[22] Filed: May 22, 1974

[21] Appl. No.: 472,174

Related U.S. Application Data

[63] Continuation of Ser. No. 280,232, Aug. 14, 1972, abandoned.

[52] U.S. Cl. .................. 260/448.2 E; 260/448.8 R
[51] Int. Cl.² ......................... C07F 7/18; C07F 7/08
[58] Field of Search .............. 260/448.2 E, 448.8 R

[56] References Cited
UNITED STATES PATENTS

| | | |
|---|---|---|
| 3,278,484 | 10/1966 | Tesoro ..................... 260/448.8 R X |
| 3,627,802 | 12/1971 | Lee ............................. 260/448.2 E |
| 3,632,826 | 1/1972 | Berger ..................... 260/448.2 E X |

*Primary Examiner*—Paul F. Shaver
*Attorney, Agent, or Firm*—George A. Skoler

[57] ABSTRACT

This invention is concerned with the manufacture of mercapto substituted silicon compounds by the decomposition of thio ether substituted silicon compounds. Acid catalysts, such as Friedel-Craft catalysts and halides of transition metals, greatly assist this decomposition.

10 Claims, No Drawings

PROCESS FOR MAKING MERCAPTO SUBSTITUTED SILICON COMPOUNDS

This is a continuation of application Ser. No. 280,232 filed Aug. 14, 1972, now abandoned.

This invention relates to a novel process for making mercapto alkyl silicon compounds. The process of this invention involves converting sulfide (or thio ether) substituted silicon compounds in a relatively simple and efficient manner to produce mercapto alkyl silicon compounds.

The process of this invention involves converting known materials in a simple and facile manner in essentially quantitative yields to a mercapto substituted silicon compound such as silanes, siloxane homopolymers and siloxane copolymers.

Mercapto substituted silicon compounds are known in the art. In most cases, they have been made by two processes. One involves the addition of hydrogen sulfide to an ethylenically unsaturated radical bonded directly to silicon. This is illustrated in the reaction of hydrogen sulfide with a vinyl substituted silane. Another method for the manufacture of mercapto substituted silicon compounds involves the reaction of sodium mercaptide with a chloroalkyl or chloroaryl silicon compound. Both methods suffer from a number of processing difficulties. For example, the reaction of hydrogen sulfide with the ethylenically unsaturated silicon compound suffers from the requirement that a large excess of hydrogen sulfide must be employed in order to effect the reaction. Excesses greater than 400% of the stoichiometric quantity necessary to form the mercapto substitution are required. In addition, the reaction also causes the formation of a relatively large quantity of the bis-silylorgano sulfide of the ethylenically unsaturated silicon compound. Yields of such sulfide can run as high as about 25 weight percent of the reaction product.

With respect to the reaction between sodium mercaptide and the chloro alkyl or aryl silicon compounds to form the mercaptans, there are a number of processing difficulties. For example, the yield of chloroalkyl or chloroaryl silicon compound that one can obtain is relatively low, particularly when making a chloroalkyl silicon compound such as a gamma-chloropropyl silicon compound by the reaction of allyl chloride and a silicon hydride. Usually, the yield of desired chlorinated product does not exceed about 60 weight percent, based on the weight of the starting silicon hydride material. In addition, since sodium mercaptide is a solid, a substantial quantity of solvent is needed in the process. Usually the solvent is methanol and the methanol content is about 50 weight percent or more of the sodium mercaptide-methanol mixture. The reaction between sodium mercaptide and chlorinated alkyl or chlorinated aryl silicon compound results in the formation of sodium chloride. Sodium chloride is a corrosive material and its removal adds to the cost of the process.

There is described herein a process to produce such mercaptans which essentially avoids the type of problems characterized above.

The invention of this process involves the decomposition of thio ether (or sulfide) substituted silicon compounds to produce corresponding mercapto alkyl silicon compounds. The thio ether compound which can be converted in accordance with this invention to the corresponding mercapto alkyl compound is one which possesses a sulfur atom bonded to a primary carbon atom which is part of the alkyl group directly connected to the silicon atom and the other valence of the sulfur atom is bonded to a secondary or tertiary carbon atom. This relationship is very important in order to achieve a mercapto alkyl silicon compound. Illustrative of this characterization are the organo silicon compounds of the following formula:

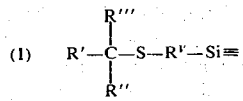

wherein R' and R'' are monovalent hydrocarbon radicals; R''' is hydrogen or a monovalent hydrocarbon radical; $R^V$ is a divalent hydrocarbon radical in which the carbon atom thereof bonded to sulfur is methylene, and, preferably, contains 2–10 carbon atoms; and the Si free valences are bonded to one or more of hydrolyzable groups, monovalent organic radicals and oxygen which in turn is bonded to other silicon atoms to form a siloxane.

The thio silicon compounds and their methods of manufacture are described in, e.g., U.S. Pat. No. 3,170,970, patented Feb. 23, 1965, U.S. Pat. No. 2,835,690, patented May 20, 1958, and U.S. Pat. No. 3,078,292, patented Feb. 19, 1963.

The thio substituted silicon compounds are formed by the addition of a mercaptan of the formula:

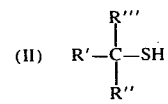

wherein R', R'' and R''' are defined above, to an ethylenically unsaturated silicon compound, such as one characterized by the following:

wherein $R^{VI}$ is a monovalent alkenyl containing radical which is terminally unsaturated, at least one of the three (3) valences of the silicon atom are bonded directly to hydrolyzable groups such as halide, alkoxy, acyloxy, aryloxy, and the like, and/or oxygen which in turn is bonded to other silicon atoms to form a siloxane. The remaining free valences of the silicon atoms are bonded by carbon to silicon bonds monovalent organic groups.

Illustrative of the thio ethers useful in the practice of this invention include those encompassed by the formula:

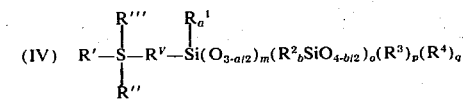

wherein R, R', R'', R''' and $R^V$ are described above, $R^1$ is any monovalent organic group bonded to silicon by a carbon to silicon bond and typically contains not more than about 12 carbon atoms; $R^2$ can be hydrogen and/or $R^1$; $R^3$ is bonded directly to silicon and is a hydrolyzable and/or condensible radical such as halide, hydroxyl, alkoxy, aryloxy, acyloxy, and the like; $R^4$ is directly bonded to siliconbonded oxygen and may be hydrogen, alkyl, aryl, acyl and the like, $m$ is 0 or 1; $a$ is 0, 1 or 2; $b$ is 0, 1, 2 or 3; $o$ is 0 or 1; $p$ is equal to 3-a when $m$ is 0 and when $m$ is 1, $p$ is 0; and $q$ is 0 when $p$ is equal to 3-a and $q$ is 0 or a positive number when $m$ is 1.

Illustrative of $R^1$ is any monovalent organic radical such as alkyl (e.g., methyl, ethyl, pentyl, dodecyl, octadecyl, 2-ethylhexyl, and the like), cycloalkyl (such as cyclobutyl, cyclohexyl, 4-methylcyclohexyl, and the like), aryl (such as phenyl, 2-naphthyl, 2-anthracyl, biphenyl, and the like), alkaryl (such as 4-methylphenyl, 2,4-diethylphenyl, 4-dodecylphenyl, and the like), aralkyl (such as phenylethyl), alkenyl (such as vinyl, allyl, 3-butenyl, oleyl, and the like), alkaldienyl (such as 1-butadienyl-1,4,1-octadecatrienyl-9, 11, 13, 1-neoprenyl, and the like), cycloalkenyl (such as 3-cyclohexenyl), haloalkyl (such as chloromethyl, gamma-chloropropyl, 3,3,3-trifluoropropyl, perfluoropropyl), haloaryl (such as 4-chlorophenyl), cyanoalkyl (such as beta-cyanoethyl, gamma-cyanopropyl and the like); cyanoaryl (such as 4-cyanophenyl); cyanocycloalkyl (such as 4-cyanocyclohexyl, 3-cyanocyclopentyl, and the like); and the like.

Illustrative of alkoxy, acyloxy, and aryloxy, such as mentioned above and characterized by $R^3$ or $R^4$ when $q$ is a positive number, are for example methoxy, ethoxy, propoxy, dodecyloxy, isopropoxy, and the like; phenoxy, naphthyloxy, biphenyloxy, and the like, formyloxy, acetyloxy, proprioxy, and the like.

The resulting mercaptan has the following formula:

(V) 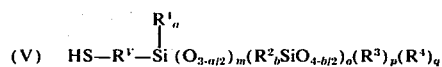

as above defined.

Illustrative of useful alkenyl silicon compounds of Formula III are the following:

ViCiCl$_3$, ViSiMeCl$_2$, ViSiMe$_2$Cl, ViSiMe$_3$, ViSiPhCl$_2$, ViSiPh$_2$Cl, ViSiPh$_3$, ViSi(OMe)$_3$, ViSiMe(OMe)$_2$, ViSiMe$_2$OMe, ViSi(OCH$_2$CH$_2$OCH$_3$)$_3$, Vi$_2$Si(OMe)$_2$, ViSiMe(OCH$_2$CH$_2$OCH$_3$)$_2$, ViSiMe$_2$OCH$_2$CH$_2$OCH$_2$CH$_3$, ViSiO$_{1.5}$, AllSiCl$_3$, AllSiMeCl$_2$, All$_2$Si(OMe)$_2$, All$_3$SiOMe, Vi$_3$SiOMe, Vi$_3$SiCl,

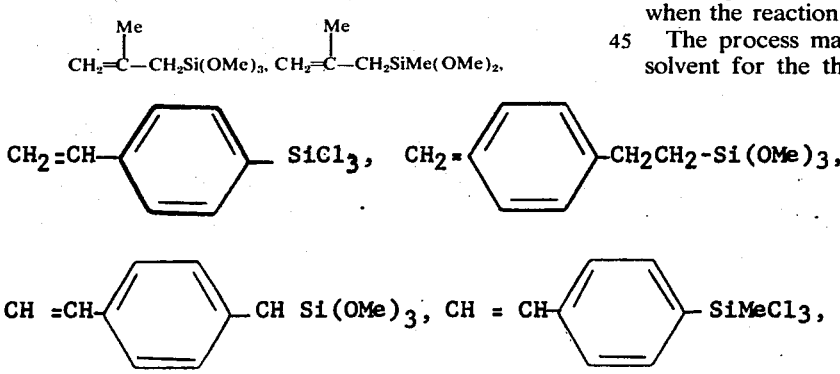

[Me$_3$Si]$_2$O-[ViMeSiO]$_{1.2}$[Me$_2$SiO]$_{454}$, HO-[ViMeSiO]$_5$-[EtPhSiO]$_{14}$-H, [ViMeSiO]$_4$, CH$_2$=CH+CH$_2$+$_2$Si(OCH$_2$CH OCH$_3$)$_3$, CH$_2$=CH+CH$_2$+$_4$SiCl$_3$, and the like. In the above formulae and elsewhere in this application, "Me" means methyl, "Ph" means phenyl, "All" means allyl, "Vi" means vinyl and "Et" means ethyl.

Illustrative of the mercaptans characterized by Formula II which provide thio ether of Formula I are, for example, isopropyl mercaptan, sec.-butyl mercaptan, sec.-pentyl mercaptan, sec.-hexyl mercaptan, sec.-dodecyl mercaptan, tertiary butyl mercaptan, tertiary amyl mercaptan, tertiary hexyl mercaptan, tertiary nonyl mercaptan, cumyl mercaptan, 2-phenyl-2-mercaptoethane, 2-biphenyl-2-mercapto propane, 4-cyclohexyl-4-mercapto nonane, 3-methyl-3-mercapto octadecane, and the like.

The decomposition of the sulfides of Formula I to form the corresponding mercaptan is effected in the presence of an acid catalyst such as those characterized as Friedel-Crafts catalysts and halides of transistion metals, such as zinc chloride, aluminum chloride, ferric chloride, boron trifluoride, boron trifluoride-etherate, boron trichloride, aluminum bromide, zinc iodide, and the acidic halides (chlorides, bromides, iodides) of transition metals such as titanium, zirconium, hafnium, chromium, molybdenum, tungsten, vanadium, niobium, tantalum, manganese, rhenium, iron, ruthenium, osmium, cobalt, rhodium, iridium, nickel, palladium, platinum, copper silver and gold. The preferred catalysts are, for example, zinc chloride, stannic chloride and cobalt chloride.

The amount of catalyst used is not narrowly critical. That amount which is sufficient to decompose the thio ether at a desired rate and yield of produced mercapto compound is adequate. Usually, the amount of catalyst is not less than about 0.01 weight percent to not more than about 5 weight percent, based on the weight of the thio ether.

The decomposition of the thio ether to the mercaptan can be achieved at a temperature ranging from as low as about 100°C. to about 300°C. though, preferably, at least about 120°C. to about 250°C.

The reaction may be effected in the absence of a solvent for the thio ether and the catalyst. The reaction may be effected in the vapor phase by heating the thio ether to a temperature which causes it to be vaporized and passing the vapors through a zone containing the acid catalyst. The acid catalyst may be placed upon a support material, preferably one that is inert to the reaction such as, for example, calcium chloride, silica gel, alumina and carbon.

When the reaction is carried out in the vapor phase, the temperature employed typically ranges higher than when the reaction is carried out in the liquid phase.

The process may be effected in the presence of a solvent for the thio ether provided that the solvent selected does not interfere with the reaction; in other words, it is inert to the thio ether and the resulting mercaptan. Illustrative of suitable solvents employable in the process of this invention include, by way of example, o-dichlorobenzene, biphenyl and high boiling hydrocarbons such as dodecane, and the like.

This process provides not only high yields and conversions of known materials to a mercapto-substituted silicon compound but also can be effected with a one to one molar ratio of reactants without the use of a special high pressure reactor. This process distinguishes from the free radical catalyzed addition of hydrogen sulfide to vinyl silanes which requires a four-fold excess of hydrogen sulfide and a high pressure reactor with an operating pressure of at least 700 psig. The process of this invention generates no thio ether by-products, such as $Cl_3SiCH_2CH_2SCH_2CH_2SiCl_3$, which is produced in about 30 weight percent in the addition reaction of $H_2S$ to $ViSiCl_3$. This process generates no solid by-products, which is an advantage over the reaction of sodium mercaptide with a chloroalkyl or chloroaryl silicon compound. The sodium mercaptide method generates a mole of sodium chloride per mole of product. Also this process requires no solvents of any kind while the sodium mercaptide method requires about 50 weight percent or more of methanol.

EXAMPLE I

This example describes two methods for effecting the addition of tert-butyl mercaptan to vinylchlorosilane by use of a free radical generating source.

(A) Ultraviolet (UV) Light

Into a 500-ml three-necked flask equipped with a condenser, a thermometer, a magnetic stirrer and a quartz immersion well were charged 258 g. (1.6 moles) of vinyltrichlorosilane and 144 g. (1.6 moles) of tert-butyl mercaptan. A small UV lamp (shortwave) was placed in the quartz immersion well. The reaction mixture was irradiated with UV light for 12 hours. The contents were fractionally distilled to give 266 g. of pure $Cl_3Si$-$CH_2CH_2SC(CH_3)_3$, b.p. 66°C./2.3 mm Hg. Conversion of vinyltrichlorosilane to products was 80 percent. Yield of $Cl_3SiCH_2CH_2SC(CH_3)_3$ was 83 percent, based on vinyltrichlorosilane reacted.

(B) Azobisisobutyronitrile Catalyst

Into a 300 ml. stainless steel reactor were charged 161.5 g. of vinyltrichlorosilane (1.0 mole), 90.2 g. tert-butyl mercaptan (1.0 mole) and 1 g. of azobisisobutyronitrile catalyst (0.4 weight percent, based on total charge). The contents were heated to 80°–90°C. for 5 hours. Internal pressure rose to a maximum of 25 psig. Heating was stopped and 250 g. of reaction products were collected. Vapor phase chromatography analysis showed a clean reaction with 76 percent conversion of vinyltrichlorosilane to products. The yield of $Cl_3SiCH_2CH_2SC(CH_3)_3$ was 90 percent.

EXAMPLE II

This example shows the addition of tert-butyl mercaptan to vinyltrichlorosilane in the presence of a transition metal halide-sulfur catalyst.

Into a 300 ml. stainless steel reactor were charged 127.5 g. (0.79 mole) of vinyltrichlorosilane, 71.2 g. (0.79 mole) of tert-butyl mercaptan, 0.4 g. (0.2 weight percent based on total charge) of cobaltous chloride and 0.8 g. (0.4 weight percent) of sulfur. The contents were heated to 120°C. to 130°C. for 9 hours. Internal pressure rose to a maximum of 45 psig and then dropped down to less than 10 psig. Heating was stopped and 199 g. of reaction product mixture were collected. Fractional distillation recovered 2.9 g. of $ViSiCl_3$ and yielded 183 g. of the thio ether product, $Cl_3SiCH_2CH_2$-$SC(CH_3)_3$, beta-(tert.-butyl thio)ethyltrichlorosilane. The product was identified by its elemental analysis, IR and nmr spectra. Conversion of $ViSiCl_3$ to product was 98 percent. The yield of $Cl_3Si$ $CH_2CH_2SC(CH_3)_3$ was 94 percent based on $ViSiCl_3$ reacted.

Refractive index of (tert-butyl thio)ethyltrichlorosilane, $Cl_3SiCH_2CH_2SC(CH_3)_3$, $N^{25}$ 1.4781.

Elemental analysis = Calculated for $C_6H_{13}Cl_3SiS$ C, 28.63; H, 5.20; Si, 11.15; S, 12.74. Found = C, 28.90; H, 5.39; Si, 10.92; S, 13.21.

EXAMPLE III

This example describes the cleavage of beta(tert.-butyl thio)ethyl trichlorosilane to beta-mercaptoethyltrichlorosilane in the liquid phase with a metal halide catalyst.

Into a 100 ml. three-necked flask equipped with a condenser, a thermometer, a magnetic stirrer were charged 88.5 g. of $Cl_3SiCH_2CH_2SC(CH_3)_3$ and 1.8 g. of anhydrous zinc chloride. The contents were heated slowly. Gaseous product was produced at 140°C. and rapidly at 165°C. The reaction temperature was kept at 170°–180°C. for 2 hours. The contents were distilled at reduced pressure. A fraction, b.p. 42°C./3.0 mm Hg, weighed 39.4 g. was collected. This fraction was shown to be betamercapoethyltrichlorosilane. About 10 percent of the starting material was recovered. This conversion of $Cl_3SiCH_2CH_2SC(CH_3)_3$ to product was 90 percent. Yield of mercaptoethyltrichlorosilane was 64 percent. The same reaction was repeated at reduced pressure of about 400 mm Hg and with hydrogen chloride, HCl, added. The yield of mercaptoethyltrichlorosilane improved significantly to 87 percent. The conversion of $Cl_3SiCH_2CH_2SC(CH_3)_3$ to product was 93 percent.

EXAMPLE IV

This example depicts the cleavage of beta-(tert-butylthio)ethyltrichlorosilane in the vapor phase with a metal halide catalyst.

A Vycor (TM) quartz hot tube reactor (¾ inch inside diameter × 36 inches length) was packed with a zinc chloride catalyst deposited on 4 to 8 mesh (U.S. Standard) particles of anhydrous calcium chloride. To the hot tube reactor were attached a preheater at one end and a receiver condenser assembly at the other. The hot tube reactor and the preheater were heated with an electric heater to 230°C. Beta-(tert-butylthio)ethyltrichlorosilane, 222 g. (0.883 mole), were charged in a dropping funnel and were fed into the preheater at a constant rate of 1.95 ml/min. Contact time was estimated at 2 to 5 seconds in the hot tube reactor. After about 2 hours of reaction time, a total of 187 g. of liquid products were collected in the receiver. Fractional distillation of the liquid condensate gave a fraction, b.p. 42°/30 mm Hg, which weighed 139 g. This fraction was found to be pure beta-mercaptoethyltrichlorosilane. It was identified by comparison with its boiling point, IR and nmr spectrum with those of an authentic sample. Conversion of starting material to products was 88 percent. Yield of beta-mercaptoethyltrichlorosilane was 91 percent based on the starting material reacted.

EXAMPLE V

The following depicts the cleavage of beta-(tert-butylthio)ethyltrichlorosilane with aluminum chloride.

Into a 100 ml. three-necked flask equipped with a thermometer, a stirrer and a water condenser were charged 20 g. of beta-(tert-butylthio)ethyltrichlorosilane and 0.4 g. (2 weight percent) of aluminum chloride (anhydrous). The contents were stirred and heated to 150°–160°C. for 2 hours. A non-condensed gas was generated and was identified as isobutylene. Vapor phase chromatographic analysis of the reaction mixture showed about 50 percent yield of beta-mercaptoethyltrichlorosilane was obtained. A number of side products (minor) were also present.

EXAMPLE VI

This example shows the cleavage of beta-(tert-butylthio)ethyltrichlorosilane with ferric chloride.

Into a 100 ml. three-necked flask equipped with a thermometer, a magnetic stirrer and a water condenser were charged 20 g. of beta-(tert-butylthio)ethyltrichlorosilane and 0.4 g. (2 weight percent) of ferric chloride (anhydrous). The contents were stirred and heated to 150°–160°C. for 2 hours. A non-condensed gaseous material was produced and was identified as isobutylene. Quantitative vapor phase chromatographic analysis of the crude reaction mixture showed about 35 percent yield of beta-mercaptoethyltrichlorosilane. A number of minor products were also present.

EXAMPLE VII

This example depicts an attempt to effect cleavage of beta-(tert-butylthio)ethyltrimethoxysilane with phosphoric acid catalyst in the vapor phase.

A glass hot tube reactor (¾ inch inside diameter by 36 inches length) was packed with phosphoric acid deposited on Kieselguhr. To this hot tube reactor were attached a preheater at one end and a receiver condenser assembly at the other. The hot tube reactor and the preheater were heated with an electric heater to 300°C. A stream of dry nitrogen was passed through the apparatus for 1 hour to remove water and air. Beta-(tert-butylthio)ethyltrimethoxysilane, $(CH_3O)_3SiCH_2CH_2SC(CH_3)_3$ was charged into the preheater through a flow meter at a constant rate of 0.65 ml/min. A non-condensed gas was detected and was identified as isobutylene by its boiling point (−9°C.). However, no liquid product was collected in the receiver after 10 ml. of $(CH_3O)_3SiCH_2CH_2SC(CH_3)_3$ had been charged. After 20 minutes of reaction time, a small amount of liquid was collected in the receiver. Vapor phase chromatographic analysis showed it was mainly methanol. After about 45 minutes of reaction time, liquid product collected in the receiver was about 90 percent unreacted starting material indicating that activity of the phosphoric acid catalyst had diminished. Results of this experiment indicated that the reactive ≡ SiO CH₃ group interacted with the phosphoric acid catalyst. As a result, the catalytic function of phosphoric acid was destroyed. Similar results were observed when beta-(tert-butylthio)ethyltrichlorosilane was used in place of the methoxy silane ester. Instead of methanol, hydrogen chloride was observed as by-product indicating that the reactive ≡ Si—Cl group also interacted with the phosphoric acid catalyst.

EXAMPLE VIII

This example attempts cleavage of beta-(tert-butylthio)ethyltrichlorosilane and beta-(tert-butylthio)-ethyltrimethoxysilane with phosphoric acid catalyst in the liquid phase.

Into a 100 ml. three-necked flask equipped with a magnetic stirrer, a thermometer and a water condenser were charged 50 g. of beta-(tert-butylthio)ethyltrimethoxysilane and 1.0 g. (2 weight percent) of phosphoric acid on Kieselguhr catalyst. The contents were heated and stirred at 280°C. for 2 hours. A small amount of isobutylene gas was observed for the first 15 minutes of heating and then ceased. Vapor phase chromatographic analysis of the reaction mixture showed a small amount of methanol was formed but most (ca. 85 percent) of the starting beta-(tert-butylthio)ethyltrimethoxysilane remained unchanged. Thus, a similar interaction of the reactive Si—O CH₃ group with the phosphoric acid catalyst also occurred in the liquid phase. As a result, the phosphoric acid catalyst was deactivated. Similar results were observed when beta-(tert-butylthio)ethyltrichlorosilane was used in place of the methoxy silane ester. In addition to some isobutylene, hydrogen chloride was detected in the gaseous product.

EXAMPLE IX

Into a 500 ml. three-necked flask were charged 108 g. (0.78 mole) 1-phenyl-ethanethiol, 126 g. (0.78 mole) vinyltrichlorosilane and 1.2 g. (0.5 weight percent) azobisisobutyronitrile catalyst. The contents were heated and stirred for 6 hours at 80°–90°C. Fractional distillation of the reaction mixture gave the product fraction, $Cl_3SiCH_2CH_2SCH(CH_3)C_6H_5$, b.p. 110°/0.53 mm Hg. Vapor phase chromatographic analysis of the distilled product (120 g.) showed it contained a mixture of alpha and beta isomers. Yield of (1-phenylethylthio)ethyltrichlorosilane was 85 percent, based on ViSiCl₃ reacted.

EXAMPLE X

Into a 100 ml. three-necked flask equipped with a condenser, a thermometer, a stirrer and a dip tube extended to the bottom of the flask were placed 50 g. (0.167 mole) of (1-phenylethylthio)-ethyltrichlorosilane and 0.5 g. of anhydrous ZnCl₂ catalyst. Hydrogen chloride was bubbled into the reaction mixture through the dip tube at about 10 ml. per minute. The contents were heated to 170°C. for 3 hours. Quantitative vapor phase chromatographic analysis of the reaction mixture showed 80 percent conversion to product with 88 percent yield of $Cl_3SiCH_2CH_2SH$. Fractional distillation of the reaction mixture gave a sample of $Cl_3SiCH_2CH_2SH$ identified by comparison of its refractive index, $N^{25}$ 1.4910, with that of an authentic sample. Heavies, 50 weight percent, remained after the distillation.

EXAMPLE XI

The following shows acid cleavage of (tert-butylthio)ethylmethyldichlorosilane to mercaptoethylmethyldichlorosilane.

Into a 250 ml. three-necked flask equipped with a condenser, a thermometer and a dip tube extended to the bottom of the flask were placed 134.5 g. (0.582 mole) of $Cl_2MeSiCH_2CH_2SCMe_3$ and 1 g. of anhydrous zinc chloride. Hydrogen chloride gas was bubbled into the reaction mixture at a constant rate of 10 ml./min. The contents were heated to 170°C. for 4 hours. Fractional distillation gave 92.5 g. of distillate, which consisted of 86 percent of mercaptoethylmethyldichlorosilane and 12 percent unreacted $Cl_2MeSiCH_2CH_2SC(CH_3)_3$. The crude distillate was redistilled to give a pure fraction of mercaptoethylmethyldichlorosilane, b.p. 40°C./3.0 mm Hg. Vapor phase chromatographic analysis showed that the mercaptoethylmethyldichlorosilane consisted of a mixture of alpha and beta isomers in ratio of 1:5.7. The isomers were identified by their nuclear magnetic resonance spectra. Refractive index, $N^{25}$ 1.4859, and elemental analyses were also recorded.

Elemental Analysis: Calculated for $C_3H_8Cl_2SiS$. C, 20.57; H, 4.60; Si, 16.02; S, 18.31. Found: C, 20.65; H, 4.84; Si, 15.95; S, 18.60.

Yield of mercaptoethylmethyldichlorosilane was 87 percent based on 90 percent conversion of the starting material to products.

I claim:
1. The process of forming mercaptoalkylsilicon compounds which comprises reacting at a temperature of about 100°C. to about 300°C. a silicon containing compound having the following radical bonded directly to a silicon atom thereof:

(I) 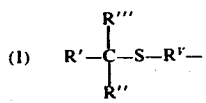

wherein R' and R'' are monovalent hydrocarbon radicals, R''' is hydrogen or a monovalent hydrocarbon radical, $R^V$ is a divalent hydrocarbon radical in which the carbon atom thereof bonded to sulfur is methylene; in the presence of an acidic Friedel-Crafts or transistion metal halide catalyst, whereby to form a silicon compound having the radical $HSR^V$— bonded directly to such silicon atom thereof.

2. The process of claim 1 wherein $R^V$ is

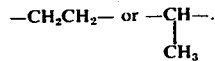

3. The process of claim 1 wherein the silicon compound has the following formula:

(IV) 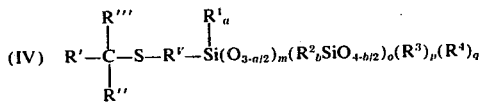

wherein R, R', R'', R''' and $R^V$ are as defined previous, $R^1$ is any monovalent organic group bonded to silicon by a carbon to silicon bond; $R^2$ can be hydrogen and/or $R^1$; $R^3$ is bonded directly to silicon and is a hydrolyzable and/or condensible radical such as halide, hydroxyl, alkoxy, aryloxy, acyloxy, and the like; $R^4$ is directly bonded to silicon-bonded oxygen and is one or more of hydrogen, alkyl, aryl, and acyl; $m$ is 0 or 1; $a$ is 0, 1 or 2; $b$ is 0, 1, 2 or 3; $o$ is 0 or 1; $p$ is equal to 3-$a$ when $m$ is 0 and when $m$ is 0; and $q$ is 0 when $p$ is equal to 3-$a$ and $q$ is 0 or a positive number when $m$ is 1.

4. The process of claim 2 wherein the Si atom has three hydrolyzable groups bonded to it.

5. The process of claim 4 wherein the hydrolyzable groups are chlorine or alkoxy.

6. The process of claim 5 wherein the hydrolyzable groups are methoxy, ethoxy, or beta-methoxyethoxy.

7. The process of claim 6 wherein the catalyst is cobalt chloride.

8. The process of claim 6 wherein the catalyst is aluminum chloride.

9. The process of claim 6 wherein the catalyst is zinc chloride.

10. The process of claim 9 wherein there is also added hydrogen chloride.

* * * * *

UNITED STATES PATENT OFFICE
CERTIFICATE OF CORRECTION

Patent No. 3,957,844    Dated May 18, 1976

Inventor(s) Jeffrey Y. P. Mui

It is certified that error appears in the above-identified patent and that said Letters Patent are hereby corrected as shown below:

Column 10, line 18, second occurrence, "when m is 0" should read -- when $\underline{m}$ is 1, $\underline{p}$ is 0 --.

Signed and Sealed this

Fourth Day of October 1977

[SEAL]

Attest:

RUTH C. MASON  
Attesting Officer

LUTRELLE F. PARKER  
Acting Commissioner of Patents and Trademarks